US005690856A

United States Patent [19]

Milleville et al.

[11] Patent Number: 5,690,856
[45] Date of Patent: Nov. 25, 1997

[54] SOLID DIACYL ORGANIC PEROXIDE DISPERSIONS

[75] Inventors: Bryce Milleville, New Fairfield, Conn.; Borys F. Schafran, Ossining, N.Y.

[73] Assignee: Akzo Nobel N.V., Arnhem, Netherlands

[21] Appl. No.: 400,146

[22] Filed: Mar. 7, 1995

[51] Int. Cl.$^6$ ................................ C01B 15/055
[52] U.S. Cl. .................. 252/186.26; 252/186.25; 252/186.42
[58] Field of Search ............... 252/186.1, 186.2, 252/186.25, 186.26, 186.42

[56] References Cited

U.S. PATENT DOCUMENTS

| | | | |
|---|---|---|---|
| Re. 28,818 | 5/1976 | Eymans et al. | 252/186 |
| 2,454,254 | 11/1948 | Kuoch et al. | 260/610 |
| 3,181,991 | 5/1965 | Leveskis | 252/430 |
| 3,182,026 | 5/1965 | Leveskis | 252/430 |
| 3,324,040 | 6/1967 | Spoor | 252/186 |
| 3,507,800 | 4/1970 | Leveskis | 252/186 |
| 3,538,011 | 11/1970 | Klanuw | 252/186 |
| 3,649,546 | 3/1972 | McCloskey | 252/186 |
| 3,723,336 | 3/1973 | Eymans | 252/186 |
| 3,795,630 | 3/1974 | Jaspers | 252/426 |
| 3,929,704 | 12/1975 | Horning | 260/29.1 |
| 4,016,328 | 4/1977 | Horning | 428/355 |
| 4,039,475 | 8/1977 | Oosterwijk | 252/431 |
| 4,151,106 | 4/1979 | Meenen | 252/186 |
| 4,155,956 | 5/1979 | Ballova et al. | 260/880 R |
| 4,255,277 | 3/1981 | Smearing | 252/186 |
| 4,255,278 | 3/1981 | Roberts et al. | 252/373 |
| 4,350,681 | 9/1982 | Fulton | 424/53 |
| 4,360,446 | 11/1982 | Smearing | 252/428 |
| 4,376,218 | 3/1983 | Izzard | 568/559 |
| 4,387,044 | 6/1983 | Sanchez et al. | 252/426 |
| 4,387,107 | 6/1983 | Klein et al. | 424/338 |
| 4,440,885 | 4/1984 | Tamosauskas | 524/57 |
| 4,440,889 | 4/1984 | Hergenrother et al. | 524/143 |
| 4,465,755 | 8/1984 | Kiritani | 430/111 |
| 4,560,495 | 12/1985 | Kato | 252/186.23 |
| 4,842,765 | 6/1989 | Satomi | 252/186.26 |
| 4,892,854 | 1/1990 | Pastorino et al. | 502/160 |
| 4,917,816 | 4/1990 | Self | 252/186.26 |
| 5,110,495 | 5/1992 | Self | 252/186.26 |
| 5,276,202 | 1/1994 | Ceh et al. | 568/559 |
| 5,334,326 | 8/1994 | Bostick | 252/186.26 |

FOREIGN PATENT DOCUMENTS

| | | | |
|---|---|---|---|
| 743092 | 12/1969 | Belgium . | |
| 0 038 988 | 11/1981 | European Pat. Off. | C08F 4/34 |
| 0 133 514 | 2/1985 | European Pat. Off. | C07C 179/15 |
| 128808 | 12/1977 | German Dem. Rep. | C07C 179/14 |
| 1618726B2 | 4/1972 | Germany . | |
| 61-130372 | 6/1986 | Japan | C08F 4/32 |
| 04288368 | 10/1992 | Japan | C08L 101/06 |
| 68059570 | 6/1970 | United Kingdom . | |
| WO 89/00173 | 12/1989 | WIPO | C08K 5/10 |

*Primary Examiner*—Shean C. Wu
*Attorney, Agent, or Firm*—Ralph J. Mancini; Louis A. Morris

[57] ABSTRACT

The present invention generally relates to solid diacyl organic peroxide formulations in liquid or paste form having improved thermal stability. The formulations generally comprise solid diacyl organic peroxide, a dispersing plasticizer having a solid organic peroxide solubility of from about 3–10%, a phlegmatizer vehicle having minimal or no solid organic peroxide solubility, and optional ingredients such as surfactants, thixotropic agents, mixtures thereof and the like.

26 Claims, No Drawings

SOLID DIACYL ORGANIC PEROXIDE DISPERSIONS

FIELD OF THE INVENTION

The present invention generally relates to solid diacyl organic peroxide dispersions in liquid or paste form having a solid organic peroxide content of 3–60% by weight.

BACKGROUND OF THE INVENTION

Diacyl peroxides are widely used as polymerization initiators, curing agents and bleaching agents. Dry peroxides of this family are, however, hazardous in dry form since they are extremely shock sensitive and flammable. By mixing these peroxides with inert substances which act as desensitizing agents, the peroxides can assume a phlegmatized state which makes the handling of these hazardous materials almost harmless. Paste and liquid formulations also allow for pumping and in some cases, spraying capabilities.

Standard organic ester plasticizers such as phthalates, benzoates and dibenzoates, phosphates, citrates, adipates, etc., are known in the use of dispersing and/or de-agglomerating solid diacyl peroxides (e.g., dibenzoyl peroxide) and are based on their ability to partially dissolve the solid diacyl peroxide agglomerate with minimal effect on its chemical and thermal stability. These plasticizers are typically employed in large amounts and allow for the dispersion of solid diacyl peroxide in standard mixing equipment (kneading mixers, planetary mixers, or high speed dispersers) giving smooth uniform dispersions in a reasonable time frame. In addition, solid diacyl peroxide can be prepared as a fine particle suspension/dispersion in plasticizer and/or water if the peroxide is (1) preground to a fine particle size (<10–20 microns) or (2) ground in-situ during the mixing phase using a homogenizer type mixer. Various commercial products of the foregoing type are available.

U.S. Pat. No. 5,334,326 describes a liquid or paste dispersion which comprises a diaroyl peroxide, a liquid alkyl ester of benzoic acid in which the alkyl group of the ester has from 8 to 12 carbon atoms, and water from 0.0 to 40% by weight. The ratio of said diaroyl peroxide to the said alkyl benzoate is from 0.3:1 to 7:1.

U.S. Pat. No. 4,255,277 describes a non-separating catalyst paste comprising a diacyl peroxide; a minor proportion of water; a finely divided calcium carbonate in an amount sufficient to prevent the composition from physically separating into its components.

U.S. Pat. No. 4,376,218 describes solid organic peroxide compositions (pastes) containing from 50% to below 70% by weight of a solid organic peroxide, such as dibenzoyl peroxide, and a combination of liquid and solid desensitizers, wherein the amount of liquid desensitizer must comprise at least 10% by weight of the composition. Examples of liquid desensitizer include liquid esters of phthalic acid, benzoic acid or phosphoric acid, a silicone oil, a liquid chlorinated hydrocarbon and the like. The solid desensitizer can be, for example, a solid ester of phthalic acid, benzoic acid or phosphoric acid, a solid chlorinated hydrocarbon or a salt of a higher fatty acid, and is included in the composition in preferred amounts of less than 20% by weight.

U.S. Pat. No. 3,723,336 discloses a non-separating composition consisting of 20 to 60 parts of dibenzoyl peroxide or dibenzoyl peroxide having one or more substituents selected from halogen, lower alkyl or lower alkoxy;

up to 20 parts of water;

a hydrophobic reaction product of a pyrogenic silica with dimethyl dichlorosilane in an amount sufficient to prevent the composition from physically separating into its components, the composition having at least 2 parts and up to 6 parts silica; and the remainder being a chemically inert plasticizer.

U.S. Pat. No. 3,795,630 claims a chemically stable composition consisting of

20–60 parts of a free radical-generating organic peroxide; said peroxide being solid at room temperature;

up to 20 parts of water;

a hydrophobic lower alkyl substituted silica which is the reaction product of a pyrogenic silica with a lower dialkyl dichlorosilane in an amount sufficient to prevent the composition from physically separating into its components, the composition having at least 2 parts and up to 6 parts of the reaction product; and the remainder being a liquid substance which is inert to the organic peroxide and in which the peroxide is substantially insoluble, said liquid substance being composed of one or more compounds selected from the group consisting of plasticizers and organic solvents.

U.S. Pat. No. 3,538,011 discloses a stabilized composition with reduced explosiveness consisting of an organic peroxide, 20–60% by weight of a plasticizer which contains at least 70% by weight of chlorine, ethylene glycol dibenzoate, triethylene glycol dibenzoate, trimethylene glycol dibenzoate and mixtures thereof.

U.S. Pat. No. 4,039,475 describes pumpable highly concentrated aqueous suspensions of organic peroxides containing (a) nonionic emulsifiers having a maximum HLB value of 12.5 and (b) nonionic emulsifiers having a minimum HLB value of 12.5 or anionic emulsifiers.

U.S. Pat. No. 4,917,816 describes organic peroxide compositions containing (a) from 35–70% by weight solid dibenzoyl peroxide particles having a particle size of 10 microns or less, (b) water (c) a compound that produces an ionic region about the peroxide particles in the dispersion, is inert as to the peroxide, and is at least water dispersible wherein said compound is selected from the group consisting of finely divided fumed silica, a sodium salt of a condensed naphthalene sulfonic acid and a sodium salt of a polymerized carboxylic acid; (d) a defoamer; and (e) a water soluble acidic inorganic salt which is inert as to the peroxide, increases the viscosity of the dispersion, retains water of hydration upon dry down of the dispersion and possesses fire retardant properties.

The last two examples contain no dispersing plasticizer and rely on particle size reduction equipment to achieve a physically stable suspension/dispersion. The remaining compositions employ large amounts of plasticizers to disperse the solid peroxide based on their ability to partially dissolve the peroxide without affecting the chemical and thermal stability of the peroxide.

A system has now been discovered whereby a highly stable dispersion/suspension of solid diacyl organic peroxides can be prepared with the minimal use of plasticizers. The formulation of the present invention has increased thermal stability due to reduced solvation of the peroxide and allows the use of secondary phlegmatizing vehicles having no or minimal dispersing/solvating ability for the peroxide without the necessity of particle size reduction equipment. Further, in products comprising dibenzoyl peroxide the amount of free benzene in the final product over time caused by the slow decomposition of dibenzoyl peroxide is substantially reduced which, in turn, is related to the superior thermal stability of the pastes/dispersions of the present invention.

SUMMARY OF THE INVENTION

The present invention generally relates to solid diacyl organic peroxide formulations in liquid or paste form. The formulations generally comprise solid diacyl organic peroxide, minimal amounts of a dispersing plasticizer, a phlegmatizing vehicle having a no or minimal solid organic peroxide solubility, and optionally, surfactants, thixotropic agents, mixtures thereof and the like.

DETAILED DESCRIPTION OF THE INVENTION

The present invention relates to solid diacyl organic peroxide formulations in a liquid or paste form. The formulations of the present invention generally comprise solid diacyl organic peroxide, minimal amounts of a dispersing plasticizer, a phlegmatizing vehicle having minimal or no solid organic peroxide solubility, and optionally, surfactants, thixotropic agents, mixtures thereof and the like.

The present invention allows one to employ small amounts of dispersing plasticizers to facilitate the breakdown of diacyl peroxide into primary particles, supplemented by the incorporation of a secondary liquid phlegmatizing vehicle having minimal or no peroxide solubility. Previously, said dispersions could not be accomplished with known mixing equipment/processes without secondary particle size reduction. The formulations of the present invention are superior to known formulations which contain only large amounts of dispersing plasticizer in that they (i) have increased thermal stability/safety properties due to the reduced solvation of the diacyl peroxide; (ii) allow the use of liquid phlegmatizing vehicles having no or minimal dispersing/solvating ability for the peroxide without the necessity of employing particle size reduction equipment; (iii) in compositions based on dibenzoyl peroxide, they have substantially reduced amount of free benzene in the final product over time caused by the decomposition of the peroxide primarily by the dispersing plasticizer; and, of course, they are commercially cheaper because less dispersing plasticizer is employed and because the need for expensive particle size reduction equipment is eliminated.

Diacyl peroxides useful in the present invention are of the general formula:

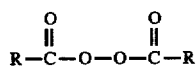

wherein R is an alkyl, cycloalkyl, aralkyl aryl or heterocyclic radical. Examples of preferred solid diacyl peroxides include but are not limited to
di-(p-chlorobenzoyl) peroxide,
di-(2,4-dichlorobenzoyl)peroxide,
acetyl benzoyl peroxide,
dilauroyl peroxide,
dibenzoyl peroxide,
benzoyl (2,4-dichloro benzoyl) peroxide,
bis(3-dibutyl phosphino-2-methyl propanoyl) peroxide,
bis(2,6-dimethyl benzoyl) peroxide,
bis(3,4-dimethoxy benzoyl) peroxide,
bis(3,3-dimethyl butanoyl) peroxide,
bis(2-methyl benzoyl) peroxide,
dicyclohexyl carbonyl peroxide,
didecanoyl peroxide,
difuroyl peroxide,
di-2-furoyl peroxide,
di-3-furoyl peroxide,
dihexanoyl peroxide,
diisobutanoyl peroxide,
diisononanoyl peroxide,
dinonanoyl peroxide,
dioctadecanoyl peroxide,
dioctanoyl peroxide,
dioleoyl peroxide,
diphthaloyl peroxide, and
disuccinoyl peroxide.

The most preferred diacyl peroxide is dibenzoyl peroxide. The dispersions of the present invention generally contain from about 3% to about 60% by weight diacyl peroxide. More preferably, dispersions according to the present invention contain from about 25% to about 60% by weight diacyl peroxide. In a most preferred embodiment, the dispersions contain from about 38% to about 57% by weight diacyl peroxide.

The dispersing plasticizer is preferably an organic medium capable of partially dissolving/de-agglomerating diacyl peroxide particles into an average particle size of from about 5–30 um when added in the lowest possible amount. Preferred dispersing plasticizers are mono- and di-organic acid esters having a diacyl peroxide solubility of from about 4–10%. Suitable dispersing plasticizers with diacyl peroxide solubility of from 4–10% include but are not limited to acetates, adipates, benzoates, citrates, hexanoates, lactates, maleates, phosphates, phthalates, sebacates, tallates and soy derivatives.

Specific examples of dispersing plasticizers include but are not limited to
1,2,3-propanetriol triacetate,
dibutylethyl adipate,
diisononyl adipate,
diisopropyl adipate,
butylphenyl benzoate,
phenyl benzoate,
naphthyl benzoate,
trimethylene glycol dibenzoate,
ethylene glycol dibenzoate,
dipropylene glycol dibenzoate,
alkyl esters of benzoic acid such as n-butyl benzoate,
methylbenzoate,
ethylbenzoate hexyl benzoate,
isobutyl benzoate,
acetyl-tri-n-butyl citrate,
tetraethylene glycol di-(2-ethyl hexoate),
triethylene glycol bis(2-ethylhexanoate),
dibutyl maleate,
dioctyl maleate,
2-ethylhexyl diphenyl phosphate,
isodecyl diphenyl phosphate,
tributylethyl phosphate,
tributyl phosphate,
alkyl benzyl phthalates,
dicyclohexyl phthalate,
diphenyl phthalate,
dimethyl phthalate,
diethyl phthalate,
diisobutyl phthalate,
butyl benzyl phthalate,
dioctyl phthalate,
diisooctyl phthalate,
polygylcol phthalate dibutyl phthalate,
di-1-nonyl phthalate,
di-isodecyl phthalate, dibutyl sebacate,
isooctyl tallate,
epoxidized soy bean oil,
and the like.

It is quite acceptable and in some cases preferable to employ mixtures of dispersing plasticizers. The most preferred dispersing plasticizers include dipropylene glycol dibenzoate, 2-ethylhexyl diphenyl phosphate, isodecyl diphenyl phosphate, alkyl benzyl phthalates, diisobutyl phthalate and alkyl benzoates wherein the alkyl chain has from eight (8) to twelve (12) carbon atoms. The most preferred benzoate ester is isodecyl benzoate. When the formulations of the present invention contain an alkyl benzoate, however, it is preferred that the ratio of diacyl peroxide:alkyl benzoate be greater than about 7:1, and more preferably, within the range of 7.1:1 to about 12.1.

The phlegmatizing vehicle is preferably water and/or an organic medium with minimal or no solvating/dispersing ability for the diacyl peroxide and its primary purpose is to act as a diluent for the peroxide/dispersing plasticizer intermediate. Water and/or aliphatic hydrocarbons, aromatic hydrocarbons, azelates (e.g. di-2-ethylhexyl azelate), adipates (e.g. dialkyl ($C_7$–$C_9$) adipate, diisodecyl adipate), oleates (e.g. n-butyl oleate), and phthalate (e.g. dioctyl terephthalate) are usefully employed as phlegmatizing vehicles. The aliphatic hydrocarbons are preferably normal or iso-paraffinic hydrocarbons such as n-paraffins, while light napthenic hydrotreated distillates are acceptable aromatic hydrocarbons. Generally, however, most hydrocarbons with a flash point of greater than about 100° F., a melting point of less than about 68° F. and a boiling point of greater than about 212° F. are employable in the present invention. Examples of such hydrocarbons include Jayflex® 210 (a hydrotreated light naphthenic distillate) and Jayflex® 215 (n $C_{15}$n-paraffinic hydrocarbon) sold by Exxon Corporation.

The dispersion of the present invention also optionally contains surfactants and/or thixotropic agents. Conventional and polymeric nonionic and anionic surfactants can be employed to provide physical stability to the formulation, whether a dispersion, emulsion or suspension. Examples of some preferred surfactants include polyethylene glycol mono- and di-esters,
polyoxyethylene sorbitan mono- and tri-esters,
polyoxyethylene-polyoxyproplyene copolymers,
sorbitan mono- and tri-esters,
polymeric fatty acid esters sold Under the trademark Hypermer by ICI.

Particularly good results have been achieved with the following surfactants.

| Product | Description | Manufacturer |
|---|---|---|
| pluronic ® p123 | polyoxypropylene-polyoxyethylene block copolymer | BASF |
| Hypermer ® B239 | polyhydroxy fatty acid-polyethylene glycol block copolymer | ICI |
| Hypermer ® 2296 | sorbitan ester/oligomer blend | ICI |
| Span ® 80 | sorbitan monooleate | ICI |
| Tween ® 80 | polyoxyethylene (20) sorbitan monooleate | ICI |
| Tergitol ® XD | butoxypolypropylene-oxypolyethyleneoxyethanol | Union Carbide |

The amount of surfactant or mixture of surfactants employed is typically in the range of about 0–10% by weight of the dispersion.

Thixotropic agents are employed in order to provide the desired rheological properties to the formulation including viscosity, anti-settling and thixotropy. Selection is also dependent upon chemical stability of the final formulation. Conventional and treated acrylic polymer, organoclay, polysaccharides such as cellulose, polyvinyl alcohol, precipitated and fumed silica, silicates, and water soluble natural gums are claimed, with their use being dependent upon the other ingredients of the formulation.

Particularly good results have been obtained with the following amorphous hydrophilic and hydrophobic fumed silicas

| Product | Description | Manufacturer |
|---|---|---|
| Cabosil M-5 | Amorphous fumed silica | Cabot Corp. |
| Cabosil TS530 | Hexamethyldisilazane, silica reaction product | Cabot Corp. |
| Cabosil TS610 | Dimethyldichlorosilane, silica reaction product | Cabot Corp. |
| Aerosil 200 | Amorphous fumed silica | Degussa Corp. |
| Aerosil R812 R812s | Hexamethyldisilazane, silica reaction product | Degussa Corp. |
| Aerosil R972 R974 or R976 | Dimethyldichlorosilane, silica reaction product | Degussa Corp. |

Thixotropic agents or mixtures of thixotropic agents are typically employed in amounts ranging from about 0–10% by weight of the dispersion.

The dispersions of the present invention generally contain dispersing plasticizer as a ratio amount based on the amount of diacyl peroxide present. While this ratio varies greatly based on the wt % diacyl peroxide contained in the dispersion and on whether the dispersion is in liquid or paste form, the amount of plasticizer required in the present invention is certainly much less than was otherwise thought possible. Typically, the ratio of diacyl peroxide:dispersing plasticizer for paste formulations is from about 3.4:1 to about 12:1, more preferably, from about 7.1:1 to about 12:1, and still more preferably, from about 7.3:1 to about 11:1. With liquid dispersions, the typical diacyl peroxide:dispersing plasticizer ratio is from about 3.4:1 to about 12:1, more preferably, about 5:1 to about 12:1, and still more preferably, from 7.1:1 to about 12:1. When the formulations of the present invention contain an alkyl benzoate, it is preferred that the ratio of diacyl peroxide:alkyl benzoate be greater than about 7:1, and more preferably, within the range of 7.1:1 to about 12:1 to 7.3:1 to 11:1. The balance of the dispersion formulation comprises phlegmatizing vehicle, surfactant, and thixotropic agent.

Additionally, the present inventors have unexpectedly found that in liquid diacyl peroxide dispersions, the thermal stability of such dispersions can be greatly enhanced if the phlegmatizing vehicle comprises water, and from about 10% by weight to about 90% by weight of at least one additional phlegmatizing vehicle selected from: aliphatic hydrocarbons, aromatic hydrocarbons, azelates, adipates, oleates and phthalates. The aliphatic hydrocarbons such as $C_{15}$ n-paraffins, aromatic hydrocarbons light napthenic hydrotreated distillates are preferred and generally provide the greatest improvement in thermal stability.

In one embodiment, the invention contemplates a stabilized dispersion in paste form which comprises 40–60% by weight solid diacyl organic peroxide; 3–18% by weight dispersing plasticizer having a solid organic peroxide solubility of about 4–10%; 2%–57% by weight phlegmatizing vehicle having minimal or no solid organic peroxide solubility; and optionally, at least one surfactant and at least one thixotropic/anti-settling agent.

In second preferred embodiment, the dispersion of the present invention comprises 48%–52% by weight solid diacyl organic peroxide; 4%–8% by weight dispersing plasticizer having a solid organic peroxide solubility of about 4–10%; 20%–48% phlegmatizing vehicle having minimal or no peroxide solubility; 0–10% by weight of at least one surfactant, and 0–10% of at least one thixotropic agent. A preferred example of such a formulation would be a 50% dibenzoyl peroxide (BPO) paste which comprises from 48%–52% by weight BPO, from 4–8% by weight isodecyl benzoate wherein the BPO:isodecyl benzoate ratio is greater than about 7.1:1, 0–10% of at least one surfactant, 0–10% of at least one thixotropic agent, and the remainder, phlegmatizing vehicle.

In a third preferred embodiment, the invention contemplates a stabilized dispersion in paste form which comprises 53–57% by weight diacyl peroxide; 4–8% by weight dispersing plasticizer; 15–43% by weight phlegmatizing vehicle having minimal or no peroxide solubility; 0–10% surfactant and 0–10% thixotropic agent. A preferred example of such a formulation would be a 55% BPO paste which comprises from 53%–57% by weight BPO, from 4–8% by weight isodecyl benzoate wherein the BPO:isodecyl benzoate ratio is greater than about 7.1:1, 0–10% of at least one surfactant, 0–10% of at least one thixotropic agent, and the remainder, phlegmatizing vehicle.

In another preferred embodiment, the invention contemplates a stabilized dispersion in liquid form which comprises 30–50% by weight diacyl peroxide; 2–15% by weight dispersing plasticizer; 15–68% by weight phlegmatizing vehicle having minimal or no peroxide solubility; and optionally, at least one surfactant and at least one thixotropic agent.

In another embodiment, the invention contemplates a stabilized dispersion in liquid form which comprises 30–50% by weight diacyl peroxide; 2–10% by weight dispersing plasticizer; 20–68% by weight phlegmatizing vehicle having minimal or no peroxide solubility; and optionally, at least one surfactant and at least one thixotropic agent, with the requirement that said phlegmatizing vehicle comprises water, and from about 10% to about 90% of aliphatic hydrocarbon, aromatic hydrocarbon, and mixtures thereof.

In a sixth preferred embodiment, the invention contemplates a stabilized dispersion in liquid form which comprises 38–42% by weight diacyl peroxide; 3–6% by weight dispersing plasticizer; 29–59% by weight phlegmatizing vehicle having minimal or no peroxide solubility; and optionally, 0–10% of at least one surfactant and 0–10% of at least one thixotropic agent. A preferred example of such a formulation would be a 40% BPO dispersion (liquid) which comprises from 38%–42% by weight BPO, from 3–6% by weight alkyl benzyl phthalate, 0–10% of at least one surfactant, 0–10% of at least one thixotropic agent, and the remainder, phlegmatizing vehicle.

Finally, the present invention contemplates a non-aqueous dispersion which comprises diacyl peroxide, at least one dispersing plasticizer, at least one phlegmatizing vehicle (as defined above, excluding water), and optionally, at least one surfactant, and at least one thixotropic agent.

The invention will now be illustrated by the following non-limiting examples.

Process Description

The dispersions of the present invention are prepared using mixing equipment generally known in the art. As a first step, dispersing plasticizer is added to wet peroxide and mixed to prepare a fine-particle sized 60–65% intermediate. Phlegmatizing vehicle is then added to produce a peroxide concentration of from about 20–55%.

Surfactant(s) and thixotropic agent(s) are added during the process at such time to produce the desired characteristics of the final formulation. No milling or other specialized equipment is necessary to produce these formulations.

PASTE FORMULATIONS

EXAMPLE 1

55% Dibenzoyl Peroxide (BPO) Paste

In this Example, the mixer was charged with BPO (BPO 75% in water), benzoate, water, and zinc stearate. A pre-product was formed after about 30 minutes of mixing. Nonionic surfactant (Tergitol XD) was then added to emulsify the oil into the water phase. After about 30 minutes, a smooth, short, uniform paste of the following composition was produced.

| Component | Weight % |
|---|---|
| BPO | 55.0 |
| Water | 32.5 |
| Isodecyl benzoate | 7.5 |
| Tergitol XD | 4.0 |
| Zinc stearate | 1.0 |

Comparative Example 2 generally describes a generic BPO paste containing large amounts of butyl benzyl phthalate as a solvating plasticizer in accordance with the prior art. Comparative Example 3 is a sample of Benox® B55-108, a commercial paste obtained from the Norac Company.

COMPARATIVE EXAMPLE 2

Generic High Dispersing Plasticizer 55% BPO Paste Formulation

| Component | Weight % |
|---|---|
| BPO | 55% |
| Water | 19 |
| Butyl benzyl phthalate | 20 |
| Tergitol XD | 5 |
| Zinc stearate | 1 |

COMPARATIVE EXAMPLE 3

High Dispersing Plasticizer 55% BPO Paste Formulation

| Component | Weight % |
|---|---|
| BPO | 55% |
| Isodecyl benzoate | 11 |
| Zinc stearate | 1 | and the remainder, surfactant and water.

Thermal Stability Testing

Diacyl peroxides will decompose when they are subjected to a sufficiently high temperature level. For formulations, the rate of decomposition depends on both the components and the temperature. The effects can be calculated using $n^{th}$ order kinetics and the Arrhenius equation. The rate of decomposition is proportional to the heat production measured with differential scanning calorimetry (DSC).

An internal ISO method (Akzo Nobel 220STAB.1) was used to compare heat production, and thus, thermal stability, of the formulations of the present invention with those of the prior art.

For this method, the temperature at which a heat production of 100 W/kg is reached was used as the isothermal temperature. This value is generally 80° C. for dibenzoyl peroxide paste and liquid formulations, and is obtained from dynamic scans at 2° C./min (50 mg sample, medium pressure sample pan).

At 80° C., isothermal scans were run for 60 minutes. Immediately thereafter, a second scan at 60° C. for thirty minutes was run, which served as a baseline. The total heat production was calculated as the difference between the heat production at 80° C. and the baseline. The moment at which heat production passed the baseline was time zero.

Data is reported at 10 minute intervals; lower heat production values are representative of greater thermal stability.

Table 1, below, shows the isothermal DSC results of a 55% BPO paste prepared in accordance with the present invention, i.e., that of Example 1, versus the 55% BPO pastes of Comparative Examples 2 and 3.

TABLE 1

Isothermal DSC Results
HEAT PRODUCTION

| 55% BPO Paste | 80° Isothermal (W/kg) | | | | | 85° C. Iso Peak (min) |
|---|---|---|---|---|---|---|
| | 10 min | 20 min | 30 min | 40 min | 50 min | |
| Example 1 | 19 | 18 | 17 | 16 | 17 | 57.3 |
| Comparative Example 2 | 50 | 50 | 50 | 50 | 51 | 8.6 |
| Comparative Example 3 | 24 | 26 | 29 | 32 | 34 | 30.3 |

Isothermal data was also measured at 85° C. and the very long time-to-peak interval for the formulation of the present invention is clearly indicative of a higher thermal stability as compared to the formulations of the prior art.

Benzene Formation

The present invention also experiences reduced benzene formation due to a decrease in the amount of dispersing plasticizer employed, and the greater thermal stability of the formulations. In order to demonstrate the effectiveness of the present invention, the rate of benzene formation was measured for two compositions; The Composition of Example A was prepared in accordance with the present invention and has a peroxide:plasticizer ratio of 11:1, while that of Comparative Example B possesses a peroxide:plasticizer ratio of 3.67:1.

EXAMPLE A

| Component | Weight % |
|---|---|
| Dibenzoyl peroxide | 55 |
| Isodecyl benzoate | 5 |
| Water | 36 |
| Tergitol ®XD | 3 |
| Zinc stearate | 1 |

COMPARATIVE EXAMPLE B

| Component | Weight % |
|---|---|
| Dibenzoyl peroxide | 55 |
| Isodecyl benzoate | 15 |
| Water | 24 |
| Tergitol ®XD | 5 |
| Zinc stearate | 1 |

Test Method

The rate of benzene formation was measured by equilibrating samples in a Dani headspace instrument followed by analysis of the headspace via GC/MS. Benzene D6 was used as an internal standard.

Specifically, 100 g–400 g of sample were placed in the bottom of a 20 ml headspace vial. Immediately thereafter, 2 ul of approximately 1 mg/ml D6-benzene in acetonitrile was added. Samples were equilibrated in the headspace instrument for periods of up to hours before analysis.

Headspace conditions were: 70° C. bath temperature, 100° C. manifold temperature, pressurized from 0–40 seconds, vented from 41–140 seconds, injected from 120–140 seconds at 2 bar, 1.8 bar on transfer line.

GC/MS conditions were: 25 m×0.25 mm 1 um DB-5 50° C. to 80° C. at 10° C./min, full scan, 15 psi on column, split flow approximate 15 ml/min.

The data which is listed in Table 3, below, clearly indicate that Exampl A containing 67% less isodecyl benzoate as dispersing plasticizer resulted in a 78% decrease in benzene formation a compared with Comparative Example B, a formulation common to prior art.

TABLE 3

Benzene Formation

| Example | Rate of Benzene Formation, ug/g BPO/min |
|---|---|
| A | 1.0 |
| B | 4.5 |

LIQUID DISPERSIONS

EXAMPLE 4

40% Dibenzoyl (BPO) Dispersion (Liquid)

BPO (75% in water), benzoate, and water were added to the mixer and blended for 30 minutes to produce a 65% intermediate product. Hydrocarbon (Jayflex® 215) and surfactant (Hypermer® B239) were then added and mixed for 10 minutes to create a dispersion of BPO in a water-in-oil emulsion. Silica (Aerosil® R974) was then added and mixed for 10 minutes, creating a thixotropic uniform liquid.

| Component | Weight % |
|---|---|
| Dibenzoyl peroxide | 40 |
| Isodecyl benzoate | 6.0 |
| Water | 16 |
| Aliphatic hydrocarbon | 32 |
| Silica | 4 |
| Surfactant | 2.0 |

EXAMPLE 5

40% BPO Dispersion (Liquid)

BPO (75% in water) and $C_7$–$C_9$ alkyl benzyl phthalate plasticizer (Santicizer® 261 purchased from Monsanto)

were added to the mixer and blended for 30 minutes to produce a 65% intermediate product. Hydrocarbon (Jayflex® 215) and surfactant (Hypermer® 2296/Tween® 80) were then added and mixed for 10 minutes to create a dispersion of BPO in a water-in-oil emulsion. Fumed hydrophobic silica (Cabosil TS530) was thereafter added and mixed for 10 minutes, creating a thixotropic, uniform liquid having the following composition.

| Component | Weight % |
| --- | --- |
| BPO | 40% |
| Water | 13 |
| Alkyl benzyl phthalate | 8 |
| Aliphatic hydrocarbon | 33 |
| Surfactant | 2 |
| Silica | 4 |

COMPARATIVE EXAMPLE 6

40% BPO Dispersion (liquid)

Benzoate and surfactant (Hypermer B239) were added to the mixer and blended for 10 minutes. Silica (Aerosilv4.22 R974) was added and mixed for an additional 10 minutes creating a thixotropic liquid. BPO (75% in water) was added last and mixed 20 minutes to produce a BPO dispersion in a water-in-oil emulsion having the following composition.

| Component | Weight % |
| --- | --- |
| Dibenzoyl peroxide | 40 |
| Isodecyl benzoate | 41 |
| Water | 13 |
| Surfactant | 3 |
| Silica | 3 |

Thermal Stability Data

Table 2, below, shows the isothermal DSC results for two 40% BPO liquid dispersions according to the present invention (Example 4 and 5) verses that of a typical formulation of the prior art ( Example 6).

TABLE 2

| Isothermal DSC Results for 40% BPO Dispersions HEAT PRODUCTION | | | | | | |
| --- | --- | --- | --- | --- | --- | --- |
| | 80° C. Isothermal (W/kg) | | | | | 85° C. Iso |
| 40% BPO Dispersion | 10 min | 20 min | 30 min | 40 min | 50 min | Peak (min) |
| Example 4 | 11 | 11 | 11 | 11 | 11 | 83.5 |
| Example 5 | 14 | 14 | 16 | 16 | 18 | 40.3 |
| Comparative Example 6 | 29 | 30 | 35 | 32 | 29 | 13.0 |

The isothermal data was also measured at 85° C. and the long time-to-peak intervals for the formulations of the present invention indicates unexpectedly superior (higher) thermal stability of the formulations of the present invention. Further, Example 4 clearly shows that when the liquid dispersions of the present invention phlegmatizing vehicles comprising water and from 10–90% aliphatic or aromatic hydrocarbon, the thermal stability of the dispersion increases dramatically.

We claim:

1. A stabilized dispersion in paste form with increased thermal stability which comprises: (1) diacyl peroxide, (2) at least one dispersing plasticizer, and (3) at least one phlegmatizing vehicle having minimal or no solid peroxide solubility, wherein the ratio of diacyl peroxide to dispersing plasticizer is in the range of about 7.1:1 to about 12:1.

2. The paste of claim 1 wherein said diacyl peroxide is of the general formula:

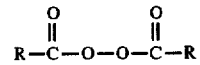

wherein R is an alkyl, cycloalkyl, aralkyl, aryl or heterocyclic radical.

3. The paste of claim 2 wherein said diacyl peroxide is selected from the group consisting of di-(p-chlorobenzoyl) peroxide, di-(2,4-dichlorobenzoyl) peroxide, acetyl benzoyl peroxide, lauroyl peroxide, dibenzoyl peroxide and mixtures thereof.

4. The paste of claim 1 wherein said dispersing plasticizer is selected from the group consisting of acetate, adipate, azelate, benzoate, butyrate, citrate, fumarate, hexanoate, maleate, oleate, phthalate, phosphate, sebacate or tallate esters, alkyl benzyl phthalates and mixtures thereof.

5. The paste of claim 4 wherein said dispersing plasticizer is selected from the group consisting of n-butyl benzoate, methylbenzoate, ethylbenzoate, hexyl benzoate, isobutyl benzoate, isodecyl benzoate, propylene glycol dibenzoate, 2-ethylhexyl diphenyl phosphate, isodecyl diphenyl phosphate, tributylethyl phosphate, tributyl phosphate, dimethyl phthalate, diethyl phthalate, diisobutyl phthalate, butyl benzyl phthalate, dioctyl phthalate, diisooctyl phthalate, polygylcol phthalate, dibutyl phthalate, di-1-nonyl phthalate, di-isodecyl phthalate and mixtures thereof.

6. The paste of claim 5 wherein said diacyl peroxide is selected from the group consisting of di-(2,4-dichlorobenzoyl) peroxide, dibenzoyl peroxide and mixtures thereof, and said dispersing plasticizer is selected from the group consisting of 2-ethylhexyl diphenyl phosphate, isodecyl diphenyl phosphate, isodecyl benzoate, propylene glycol dibenzoate, $C_{7-9}$ alkyl benzyl phthalates, diisobutyl phthalate, butyl benzyl phthalate, alkyl benzoates mixtures thereof.

7. The paste of claim 1 wherein said phlegmatizing vehicle is water, an aliphatic or aromatic hydrocarbon with a flash point of greater than about 100° F., a melting point of less than about 68° F. and a boiling point of greater than about 212° F., adipates, oleates, phthalates and mixtures thereof.

8. The paste of claim 7 wherein said phlegmatizing vehicle is selected from the group consisting of light napthenic hydrotreated distillates, $C_{15}$ n-paraffin, water and mixtures thereof.

9. The paste of claim 1 which additionally comprises nonionic surfactants, anionic surfactants and mixtures thereof.

10. The paste of claim 1 which additionally comprises at least one thixotropic agent.

11. The paste of claim 1 wherein the ratio of diacyl peroxide dispersing plasticizer is from about 7.3:1 to about 11:1.

12. The paste of claim 11 wherein the diacyl peroxide is dibenzoyl peroxide and said dispersing plasticizer is isodecyl benzoate.

13. The paste of claim 11 which comprises 48–57% by weight dibenzoyl peroxide, 4–8% by weight isodecyl benzoate, 0–10% by weight of at least one surfactant, 0–10% by weight of at least one thixotropic agent, and 20–48% by weight of a phlegmatizing vehicle.

14. A stabilized liquid dispersion with increased thermal stability which comprises: (1) diacyl peroxide, (2) at least one dispersing plasticizer, and (3) at least one phlegmatizing vehicle which comprises water and from about 10% to about 90% by weight of an aliphatic or aromatic hydrocarbon with a flash point of greater than about 100° F., a melting point of less than about 68° F. and a boiling point of greater than about 212° F., adipates, oleates, phthalates or mixtures therefore, and optionally, at least one surfactant and at least one thixotropic agent, wherein the ratio of diacyl peroxide to dispersing plasticizer is in the range of 3.4:1 to 12:1.

15. The dispersion of claim 14 wherein said diacyl peroxide is selected from the group consisting of di-(p-chlorobenzoyl) peroxide, di-2,4-dichlorobenzoyl) peroxide, acetyl benzoyl peroxide, lauroyl peroxide, dibenzoyl peroxide and mixtures thereof.

16. The dispersion of claim 14 wherein said dispersing plasticizer is selected from the group consisting of acetate, adipate, azelate, benzoate, butyrate, citrate, fumarate, hexanoate, maleate, oleate, phthalate, phosphate, sebacate, alkyl benzyl phthalates, tallate esters and mixtures thereof.

17. The dispersion of claim 14 wherein said diacyl peroxide is selected from the group consisting of di-(2,4-dichlorobenzoyl) peroxide, dibenzoyl peroxide and mixtures thereof, and said dispersing plasticizer is selected from the group consisting of 2-ethylhexyl diphenyl phosphate, isodecyl diphenyl phosphate, diisobutyl phthalate, butyl benzyl phthalate, isodecyl benzoate, propylene glycol dibenzoate, $C_{7-9}$ alkyl benzyl phthalates and mixtures thereof.

18. The dispersion of claim 14 wherein said phlegmatizing vehicle is from the group consisting of light napthenic hydrotreated distillates, $C_{15}$ n-paraffin, water, di-2-ethylhexyl azelate, dialkyl ($C_7$–$C_9$) adipate, diisodecyl adipate, n-butyl oleate, dioctyl terephthalate and mixtures thereof.

19. The dispersion of claim 14 which comprises from about 38% to 42% weight diacyl peroxide, from about 3% to about 9% by weight dispersing plasticizer, from about 29% to about 59% by weight phlegmatizing vehicle, 0–10% by weight of at least one surfactant, and 0–10% by weight of at least one thixotropic agent, wherein said phlegmatizing vehicle comprises water and from about 10% to about 90% by weight of an aliphatic or aromatic hydrocarbon with a flash point of greater than about 100° F., a melting point of less than about 68° F. and a boiling point of greater about 212° F., adipates, oleates, phthalates and mixtures thereof.

20. The dispersion of claim 19 wherein said phlegmatizing vehicle comprises water and 10–90% by weight of aromatic or aliphatic hydrocarbons comprising light napthenic hydrotreated distillates $C_{15}$ n-paraffins and mixtures thereof.

21. The dispersion of claim 20 wherein said diacyl peroxide is dibenzoyl peroxide, said dispersing plasticizer comprises a $C_8$–$C_{12}$ alkyl benzoate ester, and said phlegmatizing vehicle comprises water and from about 10% to about 90% Jayflex® 210, Jayflex® 215 and mixtures thereof.

22. The dispersion of claim 14 wherein the ratio of diacyl peroxide to dispersing plasticizer is in the range of about 7.1:1 to about 12:1.

23. The dispersion of claim 22 wherein said dispersing plasticizer comprises a $C_8$–$C_{12}$ alkyl benzoate ester, and said phlegmatizing vehicle is selected from the group consisting of water, light napthenic hydrotreated distillates, $C_{15}$ n-paraffin, di-2-ethylhexyl azelate, dialkyl ($C_7$–$C_9$) adipate, diisodecyl adipate, n-butyl oleate, dioctyl terephthalate and mixtures thereof.

24. The stabilized dispersion of claim 14 which comprises from about 38–52% by weight dibenzoyl peroxide; from about 2–15% by weight dispersing plasticizer which comprises isodecyl benzoate; from about 0–10% by weight of at least one surfactant, from about 0–10% by weight of at least one thixotropic agent, and from about 29–59% by weight of at least one phlegmatizing vehicle.

25. A stabilized, non-aqueous liquid dispersion with increased thermal stability which comprises: (1) diacyl peroxide, (2) at least one dispersing plasticizer, and (3) at least one phlegmatizing vehicle having minimal or no solid peroxide solubility selected from the group consisting of aliphatic or aromatic hydrocarbon with a flash point of greater than about 100° F., a melting point of less than about 68° F. and a boiling point of greater than about 212° F., adipates, oleates, phthalates and mixtures thereof.

26. The dispersion of claim 25 wherein said diacyl peroxide is dibenzoyl peroxide and said phlegmatizing vehicle is selected from the group consisting of light napthenic hydrotreated distillates $C_{15}$ n-paraffin, di-2-ethylhexyl azelate, dialkyl ($C_7$–$C_9$) adipate, diisodecyl adipate, n-butyl oleate, dioctyl terephthalate and mixtures thereof.

* * * * *